United States Patent [19]
Gifford et al.

(10) Patent No.: US 11,111,489 B1
(45) Date of Patent: Sep. 7, 2021

US011111489B1

(54) MULTIPLEXED TESTING OF LYMPHOCYTES FOR ANTIGEN SPECIFICITY

(71) Applicant: Think Therapeutics, Inc., Newton, MA (US)

(72) Inventors: David Gifford, Newton, MA (US); Brandon Carter, Cambridge, MA (US)

(73) Assignee: Think Therapeutics, Inc., Newton, MA (US)

(*) Notice: Subject to any disclaimer, the term of this patent is extended or adjusted under 35 U.S.C. 154(b) by 0 days.

(21) Appl. No.: 17/142,745

(22) Filed: Jan. 6, 2021

(51) Int. Cl.
C12N 15/10 (2006.01)
C40B 30/04 (2006.01)

(52) U.S. Cl.
CPC ..... *C12N 15/1037* (2013.01); *C12N 15/1089* (2013.01); *C40B 30/04* (2013.01)

(58) Field of Classification Search
None
See application file for complete search history.

(56) References Cited

U.S. PATENT DOCUMENTS

| | | | | |
|---|---|---|---|---|
| 10,066,265 | B2 * | 9/2018 | Klinger et al. | C12Q 1/6881 |
| 10,077,478 | B2 | 9/2018 | Faham et al. | |
| 2012/0196762 | A1 * | 8/2012 | Paradis | G01N 33/502 506/9 |
| 2018/0282808 | A1 | 10/2018 | Milla et al. | |

OTHER PUBLICATIONS

Klinger et al., "Identification of Antigen-Specific T Cell Receptors Using a Combination of Immune Assays and Immune Receptor Sequencing," PLoS ONE 2015, 10(10):e0141561. (Year: 2015).*
Ashby, "W. Ross Ashby's Journal: Zato-coding", Sep. 22, 1960, pp. 6208-6222. 8 pages.(http://www.rossashby.info/journal/page/6208.html.).
Binladen et al., "The use of coded PCR primers enables high-throughput sequencing of multiple homolog amplification products by 454 parallel sequencing," PLoS One, Feb. 14, 2007, ;2(2):e197. 9 pages.
Bowyer et al., "Activation-induced markers detect vaccine-specific CD4+ T cell responses not measured by assays conventionally used in clinical trials," Vaccines, 6(3), 50, Jul. 31, 2018. 19 pages.
De Simone et al., "Single Cell T Cell Receptor Sequencing: Techniques and Future Challenges," Frontiers in Immunology, Jul. 18, 2018, 9:1638. 7 pages.
Emerson et al., "Immunosequencing identifies signatures of cytomegalovirus exposure history and HLA-mediated effects on the T cell repertoire," Nature Genetics, May 2017, 49(5), pp. 659-665 and Online Methods. 10 pages.
Kim et al., "Multi-error correcting codes for a binary asymmetric channel," IRE Transactions on Circuit Theory, May 1959, 6(5), 71-78.
Kivioja et al., "Counting absolute numbers of molecules using unique molecular identifiers," Nature Methods, Nov. 20, 2011, 9(1):72-74 and Online Methods. 5 pages.
Klinger et al., "Combining next-generation sequencing and immune assays: A novel method for identification of antigen-specific T cells," PLoS One, Sep. 19, 2013, 8(9):e74231. 9 pages.
Klinger et al., "Multiplex identification of antigen-specific T cell receptors using a combination of immune assays and immune receptor sequencing," PLoS One, Oct. 28, 2015, 10(10), e0141561. 21 pages.
Lissina et al., "Priming of Qualitatively Superior Human Effector CD8+ T Cells Using TLR8 Ligand Combined with FLT3 Ligand," The Journal of Immunology (2016), 196(1), pp. 256-263, published online Nov. 25, 2015. 9 pages.
Lugosch, "Learning Algorithms for Error Correction," Masters Thesis, McGill University, Apr. 2018. 82 pages.(https://lorenlugosch.github.io/Masters_Thesis.pdf).
Mooers, "Zatocoding applied to mechanical organization of knowledge," American documentation, Jan. 1951, 2(1), 20-32. doi:10.1002/asi.509002010.
Nolan et al., "A large-scale database of T-cell receptor beta (TCRβ) sequences and binding associations from natural and synthetic exposure to SARS-CoV-2," Research Square [Preprint]. Aug. 4, 2020. 28 pages. (https://doi.org/10.21203/rs.3.rs-51964/v1).
Reiss, et al., "Comparative analysis of activation induced marker (AIM) assays for sensitive identification of antigen-specific CD4 T cells," PLoS One, Oct. 24, 2017, 12(10), e0186998. 22 pages.
Rosenberg et al., "Single-cell profiling of the developing mouse brain and spinal cord with split-pool barcoding," Science, Apr. 13, 2018, 360(6385):176-182. 8 pages.
Scheid et al., "A method for identification of HIV gp140 binding memory B cells in human blood," Journal of Immunological Methods (2009) 343(2), pp. 65-67. Available online Dec. 25, 2008.
Singh et al., "High-throughput targeted long-read single cell sequencing reveals the clonal and transcriptional landscape of lymphocytes," Nature Communications Jul. 16, 2019, 10(1):3120. 13 pages.

(Continued)

*Primary Examiner* — Kaijiang Zhang
(74) *Attorney, Agent, or Firm* — Wilmer Cutler Pickering Hale and Dorr LLP

(57) ABSTRACT

Described herein is a method for determining a lymphocyte cell receptor chain sequence specific to a unique antigen, comprising: sorting a plurality of antigens into a plurality of reaction mixtures, wherein the sorting comprises adding a unique antigen of the plurality of antigens to a unique subset of the plurality of reaction mixtures such that two different unique antigens are not added to the unique subset; contacting each reaction with a biological sample comprising a plurality of lymphocytes; separating a target lymphocyte from a subset of the plurality of lymphocytes, wherein the target lymphocyte recognizes the unique antigen; after separating the target lymphocyte, sequencing nucleic acids of the target lymphocyte to obtain the lymphocyte receptor chain sequence, wherein the sequencing is performed by single-cell sequencing; and detecting the unique antigen, wherein the detecting comprises: computing a frequency of lymphocyte cells that express the lymphocyte receptor chain sequence.

15 Claims, 2 Drawing Sheets

(56) References Cited

OTHER PUBLICATIONS

Snyder et al., "Magnitude and Dynamics of the T-Cell Response to SARS-CoV-2 Infection at Both Individual and Population Levels," medRxiv [Preprint]. Sep. 17, 2020. 33 pages.
Stahlberg et al., "Simple multiplexed PCR-based barcoding of DNA for ultrasensitive mutation detection by next-generation sequencing," Nature Protocols, Apr. 2017, 12(4), pp. 664-682.
Stubbington et al., "T cell fate and clonality inference from single-cell transcriptomes," Nature Methods, Apr. 2016, 13(4), pp. 329-332 and Online Methods. 7 pages.
Tapia-Calle et al., "A PBMC-Based System to Assess Human T Cell Responses to Influenza Vaccine Candidates In Vitro," Vaccines, Nov. 13, 2019, 7(4):181. 26 pages.
Zimmermann et al., "Antigen Extraction and B Cell Activation Enable Identification of Rare Membrane Antigen Specific Human B Cells," Frontiers in Immunology, Apr. 16, 2019, 10:829. 18 pages.
Zong et al., "Genome-wide detection of single-nucleotide and copy-number variations of a single human cell," Science, Dec. 21, 2012, 338(6114), pp. 1622-1626.

\* cited by examiner

MULTIPLEXED TESTING OF LYMPHOCYTES FOR ANTIGEN SPECIFICITY

This patent disclosure contains material that is subject to copyright protection. The copyright owner has no objection to the facsimile reproduction of the patent document or the patent disclosure as it appears in the U.S. Patent and Trademark Office patent file or records, but otherwise reserves any and all copyright rights.

INCORPORATION BY REFERENCE

All documents cited herein are incorporated herein by reference in their entirety.

TECHNICAL FIELD

The present invention relates generally to identification of lymphocyte receptors that are specific to target antigens. More particularly, the present invention relates to systems and methods of accurately identifying lymphocyte (e.g., B cell or T cell) receptor sequence chains that are specific to one or more antigens or peptides of interest.

BACKGROUND

Determining lymphocyte cell immune receptor sequences that recognize specific antigens is a complex process that results in many false positives and false negatives. U.S. Pat. Nos. 10,066,265 and 10,077,478 discloses a method for determining the sequence of one or more lymphocyte receptor chains specific to antigens of interest but fails to disclose systems and methods that can produce accurate lymphocyte receptor chain sequences (e.g., with low false positive/negative rates) specific to one or more target antigens. There exists a need for improved methods and assays for discovering lymphocyte receptor chain sequences that bind to specific antigens in pool-based detection formats and algorithms.

SUMMARY

In one aspect, the invention provides for a method for determining a lymphocyte cell receptor chain sequence, or a portion thereof, specific for two or more antigens, the method comprising: sorting a plurality of antigens into a plurality of reaction mixtures, wherein the sorting comprises adding at least two unique antigens of the plurality of antigens to at least two unique subsets of the plurality of reaction mixtures such that the at least two unique antigens are not added to any two identical subsets of the plurality of reaction mixtures, and wherein the at least two unique subsets are configured to allow a detection of two or more antigens that are specific to the lymphocyte cell receptor chain sequence, contacting each reaction mixture of the plurality of reaction mixtures with a biological sample comprising a plurality of lymphocytes, separating a target lymphocyte from a subset of the plurality of lymphocytes, wherein the target lymphocyte recognizes the at least two antigens of the plurality of antigens, sequencing nucleic acids of the target lymphocyte to obtain the lymphocyte receptor chain sequence, and detecting the two or more antigens that are specific to the lymphocyte receptor chain sequence.

In some embodiments, the lymphocyte is a T cell or a B cell. In some embodiments, separating the target lymphocyte is performed using multimer sorting. In some embodiments, the target lymphocyte is a T cell, and wherein separating the T cell is based on a marker selected from the group consisting of CD3, CD4, CD8, CD137, OX40, CD25, PD-L1, CD69, CD154, or a combination thereof. In some embodiments, the lymphocyte cell receptor chain sequence comprises a receptor chain sequence pair, and wherein the receptor chain sequence pair consists of two components of a receptor of the target lymphocyte. In some embodiments, a number of reaction mixtures comprising the two or more unique subsets is a function of a number of expected antigens that are specific to the lymphocyte receptor chain sequence. In some embodiments, the plurality of reaction mixtures comprises at least one control reaction mixture, and wherein the control reaction mixture does not contain any antigens that are added to the biological sample. In some embodiments, the target lymphocyte recognizes the at least two antigens of the plurality of antigens by binding the two or more antigens of the plurality of antigens or by binding two or more molecular complexes comprising the two or more antigens of the plurality of antigens. In some embodiments, the detecting further comprises applying, by a processor, a nearest neighbor decoding algorithm configured to determine the two or more antigens that are specific to the lymphocyte receptor chain sequence. In some embodiments, the detecting further comprises: applying, by a processor, a decoding algorithm, wherein the decoding algorithm is configured to detect the two or more antigens that are specific to the lymphocyte receptor chain sequence when the lymphocyte cell receptor chain sequence is not substantially present in at least one reaction mixture of the at least two unique subsets of the plurality of reaction mixtures. In some embodiments, the method further comprising assigning a superimposed code to each antigen of the plurality of antigens, wherein the superimposed code is configured to allow detection of the two or more antigens that are specific to the lymphocyte receptor chain sequence.

In another aspect, the invention provides for a method for determining a T cell receptor chain sequence, or a portion thereof, specific for one or more query antigens, the method comprising: sorting a plurality of first antigens into a plurality of reaction mixtures, wherein the sorting comprises adding a unique antigen of the plurality of first antigens to a unique subset of the plurality of reaction mixtures such that two unique antigens are not added to the unique subset contacting each reaction mixture with a biological sample comprising a plurality of T cells, providing conditions for a first activated T cell in at least one reaction mixture of the plurality of reaction mixtures to expand in number such that a plurality of T cells clones is formed, contacting the plurality of T cell clones with a query antigen, separating a second activated T cell and a non-activated T cell from a subset of the plurality of T cell clones, wherein the second activated T cell recognizes the query antigen, sequencing nucleic acids of the second activated T cell to obtain the T cell receptor chain sequence, and detecting the one or more query antigens specific for the T cell receptor chain sequence.

In some embodiments, separating the second activated T cell and the non-activated T cell is performed based on a marker, and wherein the marker is selected from the group consisting of CD3, CD4, CD8, CD137, OX40, CD25, PD-L1, CD69, CD154, or a combination thereof. In some embodiments, the T cell receptor chain sequence comprises a receptor chain sequence pair, and wherein the receptor chain sequence pair consists of an alpha chain sequence and a beta chain sequence. In some embodiments, the activated T cell recognizes the query antigen by binding an MHC complex comprising the query antigen. In some embodiments, the sorting further comprises applying, by a processor, an error-correcting code configured to determine which plurality of reaction mixtures each antigen of the first plurality of antigens is added to. In some embodiments, the detecting comprises applying, by a processor, a decoding algorithm, wherein the decoding algorithm is configured to detect the one or more query antigens that are specific to the lymphocyte receptor chain sequence when the lymphocyte cell receptor chain sequence is not substantially present in at least one reaction mixture of a subset of a second plurality of reaction mixtures, and wherein the at least one reaction mixture comprises the one or more query antigens.

In another aspect, the invention provides for a method for determining a lymphocyte cell receptor chain sequence, or a portion thereof, specific to a unique antigen, the method comprising: sorting a plurality of antigens into a plurality of reaction mixtures, wherein the sorting comprises adding a unique antigen of the plurality of antigens to a unique subset of the plurality of reaction mixtures such that two different unique antigens are not added to the unique subset, contacting each reaction mixture of the plurality of reaction mixtures with a biological sample comprising a plurality of lymphocytes, separating a target lymphocyte from a subset of the plurality of lymphocytes, wherein the target lymphocyte recognizes the unique antigen, after separating the target lymphocyte, sequencing nucleic acids of the target lymphocyte to obtain the lymphocyte receptor chain sequence, wherein the sequencing is performed by single-cell sequencing, and detecting the unique antigen, wherein the detecting comprises: computing a frequency of lymphocyte cells that express the lymphocyte receptor chain sequence.

In some embodiments, the lymphocyte is a T cell or a B cell. In some embodiments, the target lymphocyte is a T cell, and wherein the T cell is separated based on a marker selected from the group consisting of CD3, CD4, CD8, CD137, OX40, CD25, PD-L1, CD69, CD154, or a combination thereof. In some embodiments, the lymphocyte cell receptor chain sequence comprises a receptor chain sequence pair, and wherein the receptor chain sequence pair consists of two components of a receptor of the target lymphocyte. In some embodiments, the detecting further comprises: computing a gene expression value of a gene of the target lymphocyte. In some embodiments, the plurality of reaction mixtures comprises at least one control reaction mixture, and wherein the control reaction mixture does not contain any antigens that are added to the biological sample. In some embodiments, the target lymphocyte recognizes the unique antigen by binding the unique antigen or by binding one or more molecular complexes comprising the unique antigen. In some embodiments, the detecting further comprises applying, by a processor, a nearest neighbor decoding algorithm configured to determine the unique antigen that is specific to the lymphocyte receptor chain sequence. In some embodiments, the detecting further comprises: applying, by a processor, a decoding algorithm, wherein the decoding algorithm is configured to detect the one or more antigens that are specific to the lymphocyte receptor chain sequence when the lymphocyte cell receptor chain sequence is not substantially present in at least one reaction mixture of the unique subset of the plurality of reaction mixtures, and wherein the at least one reaction mixture comprises the one or more antigens.

In another aspect, the invention provides for a method for determining a lymphocyte cell receptor chain sequence, or a portion thereof, specific for one or more antigens, comprising: sorting a plurality of antigens into a plurality of reaction mixtures, wherein the sorting comprises adding at least two unique antigens of the plurality of antigens to at least two unique subsets of the plurality of reaction mixtures such that the at least two unique antigens are not added to any two identical subsets of the plurality of reaction mixtures, and wherein the at least two unique subsets are configured to allow a detection of one or more antigens that are specific to the lymphocyte cell receptor chain sequence, contacting each reaction mixture with a biological sample comprising a plurality of lymphocytes, separating a target lymphocyte from a subset of the plurality of lymphocytes, wherein the target lymphocyte reacts with the at least one antigen of the plurality of antigens, sequencing nucleic acids of the target lymphocyte to obtain the lymphocyte cell receptor chain sequence, and applying, using a processor, a nearest neighbor decoding algorithm configured to detect specificity of the lymphocyte cell receptor chain sequence to the one or more antigens.

In some embodiments, the lymphocyte is a T cell or a B cell. In some embodiments, the lymphocyte cell receptor chain sequence comprises a receptor chain sequence pair, and wherein the receptor chain sequence pair consists of two components of a receptor of the target lymphocyte. In some embodiments, the method further comprising contacting at least one reaction mixture of the plurality of reaction mixtures with a query antigen.

BRIEF DESCRIPTION OF THE DRAWINGS

The following figures depict illustrative embodiments of the invention.

DETAILED DESCRIPTION

Figure 1:
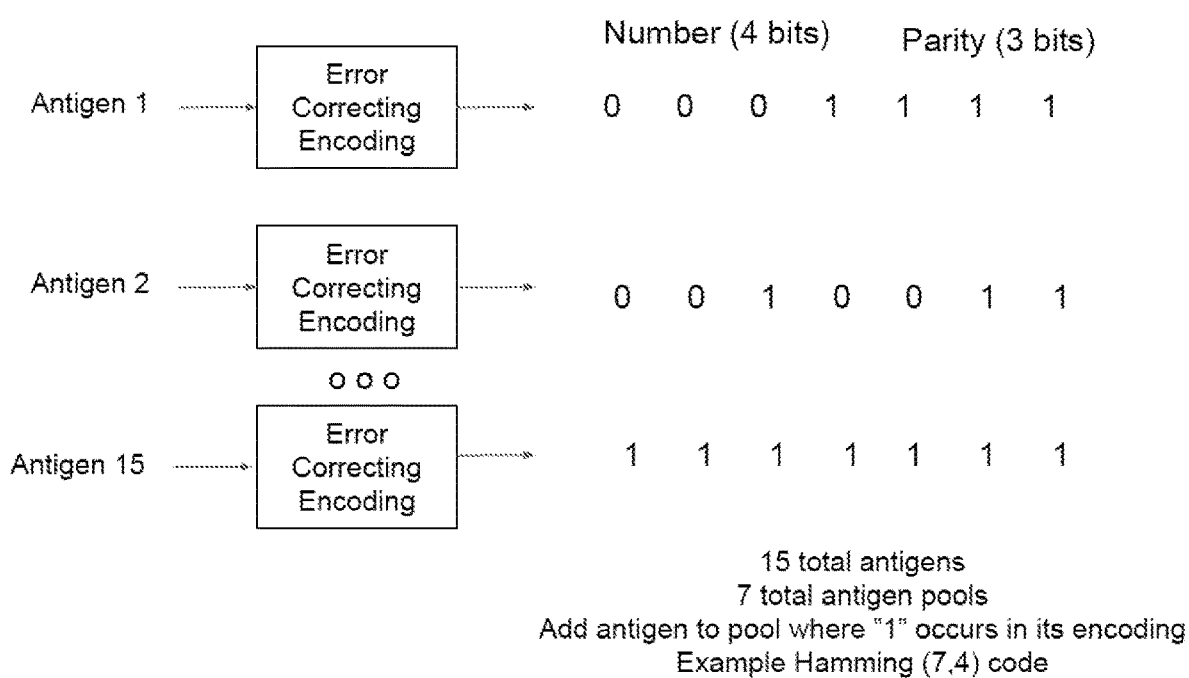
FIG. 1 illustrates a flow chart of multiplexing of antigens into samples using an error correcting code that detects errors during demultiplexing.

The systems and methods disclosed herein improve existing assays for discovering in pool-based formats the sequences of lymphocyte immune receptors that bind specific antigens directly or that bind molecular complexes (e.g., an MHC complex made of an MHC molecule and an antigen). This disclosure refers to the terms peptide(s) and antigen(s) interchangeably. In some embodiments, a "unique antigen" is an antigen with a specific amino acid sequence. In other embodiments, a "unique antigen" is an antigen derived from a specific epitope which can include multiple related peptides that are derived from that same epitope, and the "unique antigen" can therefore have more than one possible amino acid sequence. In some embodiments, a lymphocyte is an immune system cell (e.g., T cell or B cell) that displays a receptor. A lymphocyte cell receptor (LCR) is an immune receptor molecule that is present on a lymphocyte (e.g., a T cell receptor or a B cell receptor). In some embodiments, a lymphocyte receptor chain sequence means the sequence of a portion of a receptor molecule that is most variable (e.g., a CDR3 region). In some embodiments, a lymphocyte receptor sequence pair is the two chain sequences of an immune receptor's two components (e.g., for a T cell receptor, it's the alpha and beta chain sequence, for a B cell receptor it's the heavy and light chain sequence). A lymphocyte recognizes an antigen when at least one of the lymphocyte's receptors binds the antigen, when at least one of the lymphocyte's receptors bind a complex that includes an antigen (e.g., MHC complex), or the lymphocyte is activated when its receptor binds the antigen.

One advantage of the present systems and methods relates to LCR promiscuity. Certain LCR chain sequences will recognize more than one antigen that are contained in different pools (also referred to as reaction mixtures herein). Thus, a LCR sequence discovery algorithm that depends on LCR chain sequences appearing in pools/reaction mixtures unique to one antigen may fail to produce accurate results. A second advantage of the present systems and methods relates to host lymphocyte activation and non-specific markers. Lymphocytes may display native activation markers when they are isolated from animals or patients in peripheral blood mononuclear cells (PBMC) samples, and thus their activation will not be a consequence of the assay antigens. A third advantage of the present systems and methods relates to experimental noise correction. The recognition of an antigen by a lymphocyte and its subsequent selection is imperfect as a consequence of experimental noise in the selection of antigen specific lymphocyte cells and their subsequent LCR sequencing. This can happen with weak lymphocyte cell activation by an antigen that results in few selected cells and correspondingly few or no observed LCR chain sequences in an expected pool. A fourth advantage of the present systems and methods relates to LCR chain sequence count calibration. The level of lymphocyte cell recognition of an antigen and sequence discovery will vary from assay to assay and person to person. Thus, a means to normalize LCR chain sequence counts from different assays using control antigens/peptides can facilitate their direct comparison. The present disclosure employs coding and antigen controls to reduce assay errors introduced by LCR promiscuity, host lymphocyte cell activation, and experimental noise. It also provides LCR chain sequence count calibration to permit comparison of disparate assays.

In some embodiments, pooled assays are used to discover LCR chain sequences that correspond to LCRs displayed by lymphocyte cells that recognize a specific peptide/antigen. Referring to FIG. 1, K antigens (e.g., 15) are multiplexed into N antigen pools (e.g., 7), where N is less than K. K refers to the total number of antigens (or peptides) and N refers to the total number of antigen pools into which the K antigens (or peptides) are separated. Each antigen is added to a specific subset of pools, and when a LCR chain sequence (or an LCR chain sequence pair) of a lymphocyte that recognize the antigen is observed to be enriched in this subset, a conclusion is drawn that the LCR chain sequence is specific for the antigen (or peptide). In some embodiments, antigens (or peptides) are placed into pools in a manner that allows the identification of LCRs on lymphocyte cells that recognize more than one antigen (or peptide). In some embodiments, antigens (or peptides) are encoded into pools such that LCR chain sequences corresponding to an antigen (or peptide) do not have to appear (or be detected) in all pools where the antigen (or peptide) was present. In some embodiments, the ability to detect LCRs that recognize antigens (or peptides) without having all corresponding pools that contain the antigen be recognized by lymphocytes with the LCR, improves the sensitivity and accuracy of the assay.

As shown in FIG. 1, the method begins by distributing a plurality of antigens (also referred to as peptides herein) into a plurality of antigen pools. In some embodiments, antigens (e.g., antigen 1 to antigen 15 as show in FIG. 1) are distributed into pools based on a minimum Hamming distance between the binary encoding of antigen pools where they reside. Antigens (peptides) are given numbers from 1 to K (e.g., 1 to 15), and each antigen (peptide) number is encoded into N bits (e.g., each bit labeled as 0 or 1), where N is the total number of antigen pools. The N bit encoding of an antigen number may be called its code word. FIG. 1 shows an example of 15 antigens (or peptides) that are each encoded into 7 bits (of 0s and 1s), where 7 is the number of antigen pools. An antigen is placed/distributed into a given antigen pool if the bit corresponding to that antigen pool is labeled "1" in the encoding of its number, and the peptide is not placed/distributed into a given antigen pool if the bit corresponding to that antigen pool is labeled "0", as shown in FIG. 1. In some embodiments, the encoding of the antigen number uses an error correcting code, such as a Hamming code, to enforce a minimum distance in bit changes between the encodings of two antigen numbers. In some embodiments, the distance between two encodings as measured by the number of bit differences is called the Hamming distance. FIG. 1 shows the use of a "Hamming(7,4)" code that encodes up to 16 peptides into a total of 7 bits (corresponding to 7 antigen pools) resulting in a minimum Hamming distance of 3 (i.e., 4 data bits, 3 parity bits, and 7 total bits corresponding to 7 antigen pools). The use of an error correcting code can improve the sensitivity of the assay by not requiring detection of an LCR chain sequence from a lymphocyte that recognizes an antigen in every pool where the antigen is present. This can arise when, for example, by chance some pools have a small number of lymphocytes that recognize an antigen (e.g., due to imperfect separation at step 203 of FIG. 2). The use of an error correcting code improves the accuracy of the assay by allowing the detection in a biological sample of a LCR chain sequence from a lymphocyte that recognizes an antigen in one or more pools where the antigen is not present (i.e., false positive). The use of an error correcting code also improves the accuracy of the assay by allowing the lack of detection in a biological sample of a LCR chain sequence from a lymphocyte that recognizes an antigen in one or more pools where the antigen is present (i.e., false negative).

The method using the Hamming (7,4) code depicted in FIG. 1 assumes that each LCR chain sequence will be enriched in a manner specific to one antigen of the 15 antigens. In some embodiments, codes for asymmetric channels can be used when the chance of a "1" occurring by error is higher than the chance of a "0" occurring by error. In some embodiments, codes for asymmetric channels can be used when the chance of a "0" occurring by error is higher than the chance of a "1" occurring by error. In some embodiments, a "1" occurs more often than "0" when the separation of lymphocytes based on various markers is imperfect (false positive; e.g., occurring at step 203 of FIG. 2). In some embodiments, a "0" occurs more often than "1" when there are a small number of lymphocyte cells that recognize an antigen (or peptide), and thus certain pools may have an insufficient number of lymphocyte cells that recognize an antigen (or peptide) to generate a "1" signal (i.e., false negative). In some embodiments, a "1" occurs more often than "0" not due to error or chance, but rather when a lymphocyte cell recognizes more than one antigen (or peptide), and thus produced hits in pools associated with both antigens (or peptides). Examples of asymmetric codes that can perform error detection and correction optimally under these circumstances can be found in Kim and Freiman (1959), incorporated by reference in its entirety herein.

Following the assignment/sorting of peptides or antigens into antigen pools, the antigen pools are exposed to a tissue sample (e.g., PBMCs) to cause antigen pool specific antigens to be exposed to the lymphocytes contained in the tissue sample. In some embodiments, after exposure to the tissue sample, lymphocyte cells are activated by the antigens and then separated into activated and non-activated cells, and optionally also separated by other markers, as described in greater detail below. In some embodiments, after exposure to the tissue sample, lymphocyte cells bind the antigens and are then separated into antigen bound and non-bound cells, and optionally also separated by other markers, as described in greater detail below.

Figure 2:
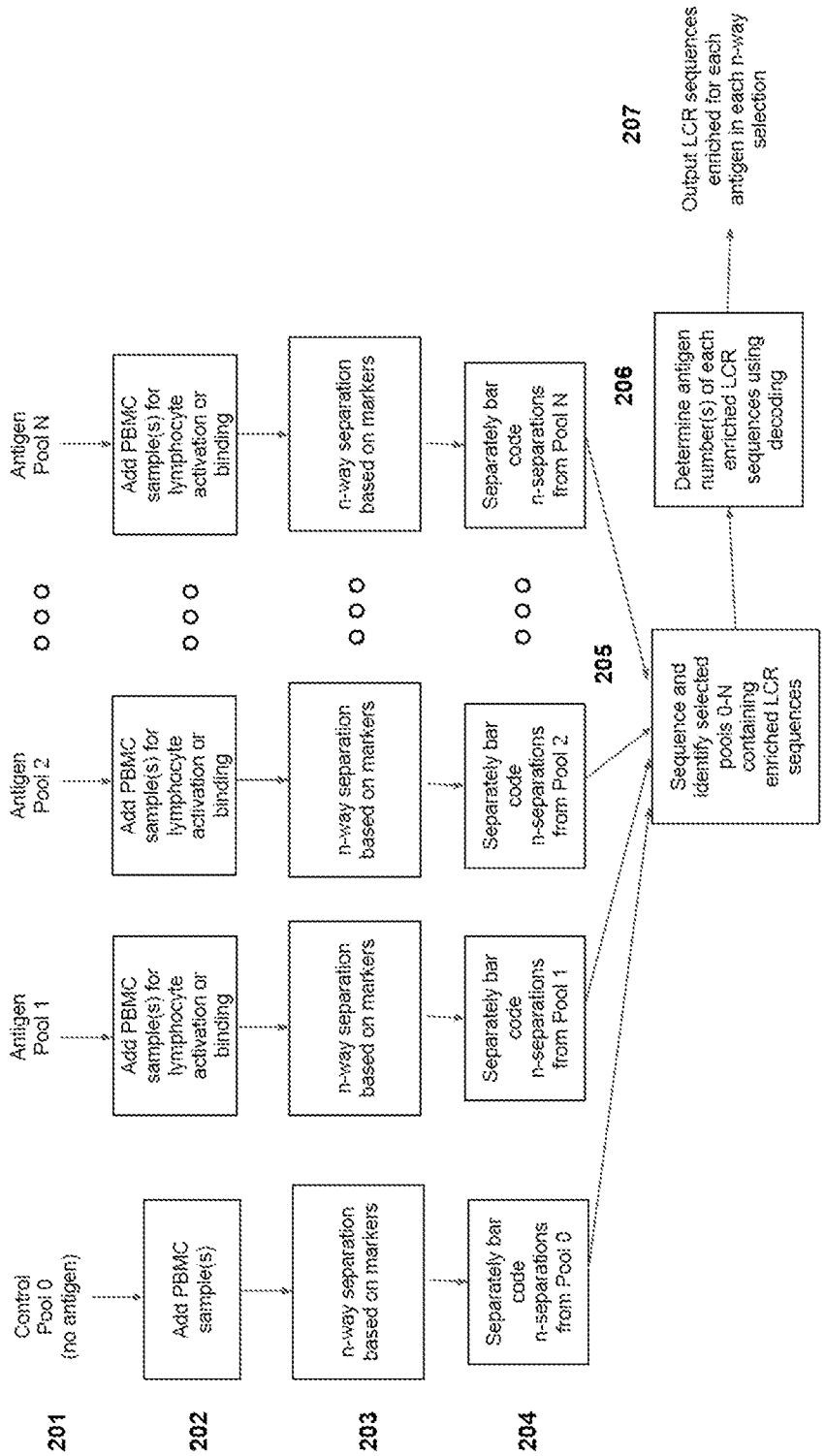
FIG. 2 illustrates a flow chart of detection of lymphocytes specific to antigens.

Referring to FIG. 2, the method begins at step 201 in which antigens (e.g., peptides) are separated into a plurality of antigen pools (e.g., antigen pool 1 to antigen pool N) using the methods described herein (e.g., see FIG. 1). In some embodiments, step 201 further includes creating a control pool ("Control Pool 0" in FIG. 1), which is free of added peptides/antigens (but may include peptides/antigens endogenous to a tissue sample, for example at step 201). At step 202, tissue samples (e.g., PBMCs) are separately exposed to the antigen pools. In some embodiments, the same tissue sample is split equally so that each antigen pool and the control pool are exposed to substantially the same tissue sample (e.g., with the same number and distribution of lymphocytes).

In some embodiments, lymphocytes that are activated by the antigen pools are allowed time to expand. In some embodiments, the antigen pools are separately re-stimulated with a query set of one or more antigens to test if the expanded lymphocytes respond to the query set of antigens. An example protocol that stimulates T cells with a first set of antigens and then queries with a second set of antigens is described by Tapia-Calle et al. (2019), which is incorporated by reference in its entirety herein. In some embodiments, LCR chain sequences that correspond to lymphocytes that recognize the query antigens are determined using the pool-based methods described herein. In some embodiments, each query antigen is assigned to the same pool as a pre-determined corresponding original pool antigen. In some embodiments, when a first plurality of antigens in the antigen pools are different than the query antigens, this assay permits the identification of lymphocyte clones that recognize both sets of antigens. For example, an increase in the frequency of a LCR chain sequence in a subset of the antigen pools in which a first antigen was added means that the LCR chain sequence is specific to that first antigen (since the corresponding lymphocytes were allowed time to expand, resulting in increased frequencies of the LCR sequence in corresponding antigen pools). A query antigen is then added to the same set of antigen pools matched to a first antigen. If the same LCR chain sequence is detected in an activated set of lymphocytes from the same group of antigen pools, a conclusion can be drawn that the LCR chain sequence recognizes both the first antigen and the query antigen. In some embodiments, query antigens are employed to test if a proposed derivative of a natural peptide, included as a first antigen, will cause expansion of lymphocyte clones that are activated by a query peptide (in which the query peptide is the natural peptide corresponding to the derivative of the natural peptide that was used as the first antigen). In some embodiments, self-peptides are employed as query antigens to test if proposed vaccine peptides (or antigens) in the first antigen pools activate lymphocytes that also are activated by self-peptides that are naturally found (e.g., query peptides are comprised of self-peptides).

In an alternative embodiment (not depicted), a tissue sample (e.g., PBMCs) is exposed to a set of first antigens (e.g., peptides) to cause expansion of lymphocytes by the first set of antigens. The activated lymphocytes are allowed time to expand. The activated and expanded lymphocytes are then separated into pools that are stimulated with a second set of pool specific antigens (e.g., query peptides). Lymphocytes are separated into activated and non-activated cells, and optionally also separated by cell type. In some embodiments, this method is used to test which specific query antigens in the antigen pools are recognized by lymphocytes activated by the first set of antigens.

In some embodiments, adjuvants are added at step 201 when the tissue sample is exposed to antigens (e.g., prior to, simultaneously with, or following exposure to the antigens). One example method of using adjuvants is described in Lissina et al. (2016), incorporated by reference in its entirety herein. In some embodiments, antigen specific responses to the use of adjuvants are observed based on the enrichment of LCR chain sequences in specific antigen pools. In some embodiments, the adjuvants added at step 201 are molecules that provide co-stimulatory signals for lymphocytes (e.g., CD28 agonists, ICOS agonists, IL-2).

In some embodiments, at step 203, lymphocytes are separated by their binding of antigens, and optionally also separated by lymphocyte cell type or other markers. For example, methods of separating T cells based on the binding of their T cell receptors (TCRs) include MHC multimer (multimer) sorting, where a multimer displays a peptide in the context of an MHC molecule (Klinger, et al., 2015). For each pool (e.g., pools 0 to N), a set of fluorescent multimers is used that collectively displays all of the antigens (or peptides) present in a pool when bound by one or more than one MHC molecule. A given pool's cells are then sorted by cells that are specific to the multimers assigned to the pool by fluorescence activated cell sorting (FACS). In some embodiments, multi-parameter FACS is used to separate each cell by multimer positive and negative cells with the addition of one or more additional markers such as CD4+ (CD4+ T Cell), and CD8+(CD8+ T Cell), or other desired markers. Methods of separating B cells include sorting B cells that are bound to an antigen in a pool, and optionally by their type as determined by cell surface markers or other means known in the art. Example methods of sorting B cells based on their binding of antigens are described in Scheid, et al., 2009 and Zimmermann, et al., 2019, which are incorporated by reference herein in their entireties In some embodiments at step 203, lymphocytes are separated into activated and non-activated cells, and optionally also separated by cell type (e.g., T cell, T cell type). In some embodiments, at step 203, activation markers that are specific for activated cells, and/or different cell types, can be used to identify and then separate cells that are activated by an antigen. In some embodiments, antigens (peptides) are added to a PBMC sample and cells in the PBMC sample take up and display the antigens (peptides) using their native MHC molecules. Assays such as Activation Induced Markers (AIM) can be used to identify activation markers (see Bowyer G, et al. and Reiss S, et al., incorporated by reference in their entireties herein). Cell markers can be extracellular or intracellular, and cell permeabilization is used to permit antibodies to recognize intracellular markers. For example, activated T cells have been identified by their cell surface OX40+CD25+ markers using AIM. The type of cell that is activated can be further discriminated with other activation markers, including CD3+(CD3+ T Cell), CD4+ (CD4+ T Cell), and CD8+(CD8+ T Cell). Other T cell activation markers known in the art can be used including CD137 and OX40, CD25, PD-L1, CD69, and CD154.

Lymphocyte cells can be physically separated by their markers at step 203 to enable the sequencing of the LCR chain sequences (at step 205, discussed in greater details below) in the physically separated cells. In some embodiments, four separations of T cells result from each pool at step 203: 1) CD8+, Activated, 2) CD8+, Not activated, 3) CD4+, Activated, and 3) CD4+, Not activated.

Cell separation at step 203 can be accomplished with bead-based methods, cell sorting-based methods, or other separation methods known in the art. In some embodiments, separation can be two-way, four-way, or more ways. In some embodiments, one or more separations for each pool are retained. Markers used for separation can include cell proteins, antigen epitopes, antigens that are fluorescently tagged, fluorescent antibodies, florescent reagents, and other methods known in the art. Marker specific antibodies can be conjugated to beads, the beads can be exposed to a population of cells, and cells containing the selected markers can be physically separated by separating the beads. When selected cells are desired that are positive for more than one antibody, bead selections can be done serially. Alternatively, selection antibodies can be conjugated with a fluorescent dye and fluorescence activated cell sorting can be employed. In some embodiments, antigens are fluorescently tagged, and sorting can be accomplished using this as one marker. Multi-parameter flow sorting can permit the separation of cell-based markers such as type (e.g., CD4, CD8) and their activation status at the same time. In some embodiments, all cell separations are retained for each antigen pool. In some embodiments, four separations of T cells result from each antigen pool: 1) CD8+, Activated, 2) CD8+, Not activated, 3) CD4+, Activated, and 4) CD4+, Not activated.

At step 204, in some embodiments, nucleic acids are extracted from each separation of cells and separately amplified using TCR chain (e.g., T cell alpha, T cell beta, or both) or B cell receptor (BCR) chain (e.g., B cell heavy chain, B cell light chain, or both) specific PCR primers for sequencing. In some embodiments, DNA is extracted from each separation for sequencing. In some embodiments, RNA is extracted from each separation and converted into DNA by reverse transcription for sequencing. In some embodiments, control nucleic acid molecules that will be amplified with one or more of the specific PCR primers are added prior to PCR amplification to each separation at one or more pre-determined concentrations to enable precise quantification of the number of LCR chain molecules present. Methods for sequencing TCR and BCR receptor sequences are described in U.S. Pat. No. 10,077,478, incorporated by reference in its entirety herein. In some embodiments, multiplex PCR is used to simultaneously amplify nucleic acid sequences originating from different LCR chains. In some embodiments, PCR primers encode bar codes that are contained in all of their product nucleic acid molecules as known in the art (Ståhlberg, et al., 2017, Binladen, et al., 2007, incorporated by reference in their entireties herein). In some embodiments, PCR primers include Unique Molecular Identifiers (UMI) to provide more accurate counting of LCR chain molecules as known in the art (Kovioja, et al., 2011, incorporated by reference in its entirety herein). In some embodiments, when two or more reads contain the same UMI or random barcode (Ståhlberg, et al., 2017) and the same other contents, only one of the reads is counted. In some embodiments, the nucleic acids derived from separations from each pool include a separation specific bar-code when prepared for sequencing in step 204. In some embodiments, the amplified nucleic acids include a pool specific bar code to permit the mixing of pools for sequencing when prepared in step 204. In some embodiments, separate nucleic acid primers specific for LCR chains (e.g., alpha or beta) are used that include a chain specific bar code to amplify nucleic acids from each pool for sequencing in step 204. In some embodiments, molecules corresponding to amplified LCR chains contain a unique molecular identifier (UMI) and three bar codes: a separation specific bar code, an antigen pool specific bar code, and a LCR chain specific bar code (e.g., alpha or beta).

At step 204, in some embodiments, single-cell based methods are used to sequence LCR chains from one or more separations. In some embodiments, methods for measuring the RNA transcriptomes of single cells can provide paired sequences of LCR chains (De Simone, et al., 2018, Singh, et al., 2019, Stubbington, et al., 2016, incorporated by reference in their entireties herein). In some embodiments, methods for sequencing the DNA of single cells can be used to produce LCR chain sequencing reads from single cells or a count of the number of cells that contain an LCR chain sequence (Zong, et al., 2012). In some embodiments, methods for measuring the RNA transcriptomes of single cells can be used that do not require the physical separation of single cells (Rosenberg, et al. 2018). In some embodiments, methods that provide mRNA transcript levels from single cells can provide transcript levels for genes that indicate lymphocyte activation or other state information that can be used in addition to, or instead of, marker information to separate cells for analysis (Singh, et al. 2019). In some embodiments, results from single-cell based methods are used in step 205 to determine, for each sequenced LCR chain, the pools in which it is enriched, as described herein. In some embodiments, the number of cells that contain an LCR chain sequence is used instead of LCR read counts in step 205. In some embodiments, mRNA transcript levels for genes from single-cell based methods are used to create or augment separations for desired analysis. Examples of mRNA expression markers include elevated expression of genes characteristic of active tissue resident cytotoxic lymphocytes, such as CCL4, NKG7, GZMA, and GZMK (Singh, et al. 2019). In some embodiments, expression or other sequencing derived markers from individual cells are used to augment or replace the separation labels (e.g., CD8+ Activated) associated with the physical separation of cells. In some embodiments, all or a portion of the cells in a pool can be analyzed by single-cell methods without separation by step 203.

At step 205, in some embodiments, the bar-coded separations are combined for sequencing on a high-throughput sequencer. The separations from each pool have their LCRs sequenced using high throughput sequencing technology. In some embodiments, adequate sequencing depth (number of raw reads from the sequencing instrument) is chosen by choosing a sequencing depth where the number of unique chains detected plateaus. At step 205, the sequencing reads from the bar-coded separations are then demultiplexed by their bar-codes for subsequent analysis. In some embodiments, decoding proceeds by identifying LCR chain sequences enriched in a desired set of physically separated pools, for example activated CD8+ cells. In some embodiments, LCR enrichment in a pool is determined by comparing LCR chain read counts observed in a desired separation (e.g., CD8+ Activated) to a function of the read counts observed in one or more other separations for the same pool (e.g., CD8+ Not activated, CD4+ Activated, CD4+ Not Activated). In some embodiments, LCR enrichment in a pool is determined by comparing LCR chain read counts observed in a desired separation (e.g., CD8+ Activated) to the read counts from one or more read counts of control nucleic acid molecules in one or more pools for the desired separation. In some embodiments, LCR enrichment in a pool is determined by comparing LCR chain read counts observed in a desired separation (e.g., CD8+ Activated) to a function of the read counts for one or more separations (e.g., CD8+ Activated) in one or more pools. In some embodiments, LCR enrichment in a pool is determined by comparing LCR chain read counts in a desired separation (e.g., CD8+, Activated) to a function of the read counts observed in one or more separations in Control Pool 0 (e.g., CD8+, Activated). In some embodiments, LCR enrichment in a pool is determined by computing a probability that the LCR chain read counts observed in a desired separation (e.g., CD8+ Activated) are drawn from a distribution computed using the read counts for one or more separations (e.g., CD8+ Activated) in one or more pools, and comparing this probability to a predetermined threshold (e.g., using standard deviation of a distribution). In some embodiments, LCR enrichment in a target pool is determined by computing the distribution of read counts observed in a desired separation (e.g., CD8+ Activated) in the target pool and comparing this distribution to one or more distributions of read counts observed in one or more separations (e.g., CD8+ Activated) in one or more other pools. In some embodiments, the enrichment of LCR chains in one or more pools is determined using statistical tests (e.g., Mann-Whitney Utest, rank-sum test, Chi-squared test, t-test, ANOVA followed by post hoc tests) or other techniques known in the art when comparing to one or more alternative pools.

In some embodiments, LCR chain read counts are normalized in each pool and separated by dividing by the total number of LCR chain read counts in that pool and that separation. In some embodiments, LCR chain read counts are normalized in each pool by dividing by the total number of LCR chain read counts in that pool. In some embodiments, for a desired separation (e.g., CD8+ Activated), all LCR chain sequence normalized read counts from all pools and all LCR chain sequences for that separation are clustered into two clusters using clustering methods known in the art (e.g. 2-means clustering). The cluster with the smaller average number of normalized read counts is labeled "0" and the cluster with the larger average number of normalized read counts is labeled "1". In some embodiments, an LCR chain sequence in a specific pool and separation is assigned a "1" or "0" based on the label of its most likely cluster assignment. In some embodiments, the LCR chain sequences assigned a "1" are considered to have been enriched.

In some embodiments, at step 205, LCR chain sequence enrichment in a pool is determined using the number of cells containing a given LCR chain sequence instead of the number of observed LCR chain sequence read counts as described herein. In single cell analysis, sequencing reads include a cell specific bar code that permits the identification of the number of cells that contain a given LCR chain sequence. In some embodiments, when single cell RNA sequencing is employed, the number of observed sequencing reads will vary from cell-to-cell depending on the number of RNA molecules present in the cell that contain an LCR chain sequence. Thus, in some instances, cell counts provide a more accurate method of determining the number of cells that contain an LCR chain sequence. In some embodiments, specific cells that contain an LCR chain sequence can be identified with one or more desired markers. In some embodiments, when single cell DNA sequencing is employed, variations and errors in the sequencing process that result in different numbers of observed LCR chain sequences for a given cell can be eliminated by using the number of cells that include a given LCR chain sequence. (e.g., based on a predetermined threshold of LCR chain sequence detection in a given cell). In some embodiments, the number of cells containing an LCR chain sequence is used for analysis in steps 205-207 in place of read counts for each LCR chain sequence. In other embodiments, bulk sequencing methods are used for read counts which can still produce accurate results. In any embodiment of the present disclosure, read counts or cell counts may be used.

At step 206, for each unique LCR chain sequence that is enriched in at least one antigen pool, a binary number corresponding to the LCR chain sequence is determined corresponding to the antigen pools where it is enriched. In some embodiments, the method proceeds by decoding the binary number with the error correcting code used for encoding (e.g., see FIG. 1). In some embodiments, a nearest neighbor decoding algorithm decodes the binary number into the antigen number with a corresponding code word with the smallest Hamming distance from the binary number. If there is more than one antigen code word with the same smallest distance, the decoding algorithm outputs an error. The result of decoding can be a valid antigen number, or it can represent an error. In some embodiments, the code used for decoding can detect errors when the pattern of enrichment does not correspond to a single antigen/peptide, and can correct errors when LCR chain sequence enrichment is corrupted by noise in samples up to the error correction limit of the code used.

At step 207, the result of the methods described herein is the output of LCR sequences enriched for each antigen (e.g., peptide) in each antigen pool. In some embodiments, the decoding of antigen number(s) corresponding to an LCR chain sequence is based on the number of read counts of the LCR chain sequence in all pools, and these read counts are interpreted by a machine learning classifier (e.g., a neural network or other statistical model) that has been trained on examples of the code employed for placing antigens (peptides) in pools. An example of training a machine learning classifier for decoding an error correcting code is described in Lugosch, 2018, incorporated by reference in its entirety herein. In some embodiments, the decoding of the antigen number(s) corresponding to an LCR chain sequence is based on the number of reads of the LCR chain sequence in all pools, and a maximum a posteriori estimator of the best antigen number(s) for the LCR chain sequence is employed. In some embodiments, the method of the present disclosure includes any combination of one or more of steps 201-207. In some embodiments, unique TCR chain sequences corresponding to alpha and beta chains are independently decoded for a desired separation. In some embodiments, unique BCR chain sequences corresponding to BCR heavy and light chains are independently decoded for a desired separation.

In some embodiments, when the same antigen number is decoded for a TCR alpha and a TCR beta chain sequence, and only one alpha chain sequence and one beta chain sequence decodes into that antigen number, they are considered to have originated from the same TCR alpha-beta receptor sequence pair that is associated with that antigen. In some embodiments, all of the TCR alpha and TCR beta chain sequences that decode to the same antigen number are ranked in each pool by their read counts where one rank list is created for alpha chains, and one for beta chains. If a TCR alpha chain and a TCR beta chain sequence in each pool have the same pool specific rank order of read counts in the alpha and beta chain rank lists, they are considered to have originated from the same TCR alpha-beta receptor sequence pair. In some embodiments, single-cell sequencing methods are used to determine TCR alpha-beta receptor sequence pairs.

In some embodiments, when the same antigen number is decoded for a BCR heavy and a BCR light chain sequence, and only one light chain sequence and heavy beta chain sequence decodes into that antigen number, they are considered to have originated from the same BCR heavy-light receptor sequence pair that is associated with that antigen. In some embodiments, all of the BCR heavy and BCR light chain sequences that decode to the same antigen number are ranked in each pool by their read counts where one rank list is created for heavy chains, and one for beta chains. If a BCR heavy chain and a BCR light chain sequence in each pool have the same pool specific rank order of read counts in the heavy and light chain rank lists, they are considered to have originated from the same BCR heavy-light receptor sequence pair. In some embodiments, single-cell sequencing methods are used to determine BCR heavy-light receptor sequence pairs.

Non-Limiting Embodiments of the Subject Matter

In one aspect, the invention provides for a method for determining a lymphocyte cell receptor chain sequence, or a portion thereof, specific for two or more antigens, the method comprising: sorting a plurality of antigens into a plurality of reaction mixtures, wherein the sorting comprises adding at least two unique antigens of the plurality of antigens to at least two unique subsets of the plurality of reaction mixtures such that the at least two unique antigens are not added to any two identical subsets of the plurality of reaction mixtures, and wherein the at least two unique subsets are configured to allow a detection of two or more antigens that are specific to the lymphocyte cell receptor chain sequence, contacting each reaction mixture of the plurality of reaction mixtures with a biological sample comprising a plurality of lymphocytes, separating a target lymphocyte from a subset of the plurality of lymphocytes, wherein the target lymphocyte recognizes the at least two antigens of the plurality of antigens, sequencing nucleic acids of the target lymphocyte to obtain the lymphocyte receptor chain sequence, and detecting the two or more antigens that are specific to the lymphocyte receptor chain sequence.

In some embodiments, the lymphocyte is a T cell or a B cell. In some embodiments, separating the target lymphocyte is performed using multimer sorting. In some embodiments, the target lymphocyte is a T cell, and wherein separating the T cell is based on a marker selected from the group consisting of CD3, CD4, CD8, CD137, OX40, CD25, PD-L1, CD69, CD154, or a combination thereof. In some embodiments, the lymphocyte cell receptor chain sequence comprises a receptor chain sequence pair, and wherein the receptor chain sequence pair consists of two components of a receptor of the target lymphocyte. In some embodiments, a number of reaction mixtures comprising the two or more unique subsets is a function of a number of expected antigens that are specific to the lymphocyte receptor chain sequence. In some embodiments, the plurality of reaction mixtures comprises at least one control reaction mixture, and wherein the control reaction mixture does not contain any antigens that are added to the biological sample. In some embodiments, the target lymphocyte recognizes the at least two antigens of the plurality of antigens by binding the two or more antigens of the plurality of antigens or by binding two or more molecular complexes comprising the two or more antigens of the plurality of antigens. In some embodiments, the detecting further comprises applying, by a processor, a nearest neighbor decoding algorithm configured to determine the two or more antigens that are specific to the lymphocyte receptor chain sequence. In some embodiments, the detecting further comprises: applying, by a processor, a decoding algorithm, wherein the decoding algorithm is configured to detect the two or more antigens that are specific to the lymphocyte receptor chain sequence when the lymphocyte cell receptor chain sequence is not substantially present in at least one reaction mixture of the at least two unique subsets of the plurality of reaction mixtures. In some embodiments, the method further comprising assigning a superimposed code to each antigen of the plurality of antigens, wherein the superimposed code is configured to allow detection of the two or more antigens that are specific to the lymphocyte receptor chain sequence.

In another aspect, the invention provides for a method for determining a T cell receptor chain sequence, or a portion thereof, specific for one or more query antigens, the method comprising: sorting a plurality of first antigens into a plurality of reaction mixtures, wherein the sorting comprises adding a unique antigen of the plurality of first antigens to a unique subset of the plurality of reaction mixtures such that two unique antigens are not added to the unique subset contacting each reaction mixture with a biological sample comprising a plurality of T cells, providing conditions for a first activated T cell in at least one reaction mixture of the plurality of reaction mixtures to expand in number such that a plurality of T cells clones is formed, contacting the plurality of T cell clones with a query antigen, separating a second activated T cell and a non-activated T cell from a subset of the plurality of T cell clones, wherein the second activated T cell recognizes the query antigen, sequencing nucleic acids of the second activated T cell to obtain the T cell receptor chain sequence, and detecting the one or more query antigens specific for the T cell receptor chain sequence.

In some embodiments, separating the second activated T cell and the non-activated T cell is performed based on a marker, and wherein the marker is selected from the group consisting of CD3, CD4, CD8, CD137, OX40, CD25, PD-L1, CD69, CD154, or a combination thereof. In some embodiments, the T cell receptor chain sequence comprises a receptor chain sequence pair, and wherein the receptor chain sequence pair consists of an alpha chain sequence and a beta chain sequence. In some embodiments, the activated T cell recognizes the query antigen by binding an MHC complex comprising the query antigen. In some embodiments, the sorting further comprises applying, by a processor, an error-correcting code configured to determine which plurality of reaction mixtures each antigen of the first plurality of antigens is added to. In some embodiments, the detecting comprises applying, by a processor, a decoding algorithm, wherein the decoding algorithm is configured to detect the one or more query antigens that are specific to the lymphocyte receptor chain sequence when the lymphocyte cell receptor chain sequence is not substantially present in at least one reaction mixture of a subset of a second plurality of reaction mixtures, and wherein the at least one reaction mixture comprises the one or more query antigens.

In another aspect, the invention provides for a method for determining a lymphocyte cell receptor chain sequence, or a portion thereof, specific to a unique antigen, the method comprising: sorting a plurality of antigens into a plurality of reaction mixtures, wherein the sorting comprises adding a unique antigen of the plurality of antigens to a unique subset of the plurality of reaction mixtures such that two different unique antigens are not added to the unique subset, contacting each reaction mixture of the plurality of reaction mixtures with a biological sample comprising a plurality of lymphocytes, separating a target lymphocyte from a subset of the plurality of lymphocytes, wherein the target lymphocyte recognizes the unique antigen, after separating the target lymphocyte, sequencing nucleic acids of the target lymphocyte to obtain the lymphocyte receptor chain sequence, wherein the sequencing is performed by single-cell sequencing, and detecting the unique antigen, wherein the detecting comprises: computing a frequency of lymphocyte cells that express the lymphocyte receptor chain sequence.

In some embodiments, the lymphocyte is a T cell or a B cell. In some embodiments, the target lymphocyte is a T cell, and wherein the T cell is separated based on a marker selected from the group consisting of CD3, CD4, CD8, CD137, OX40, CD25, PD-L1, CD69, CD154, or a combination thereof. In some embodiments, the lymphocyte cell receptor chain sequence comprises a receptor chain sequence pair, and wherein the receptor chain sequence pair consists of two components of a receptor of the target lymphocyte. In some embodiments, the detecting further comprises: computing a gene expression value of a gene of the target lymphocyte. In some embodiments, the plurality of reaction mixtures comprises at least one control reaction mixture, and wherein the control reaction mixture does not contain any antigens that are added to the biological sample. In some embodiments, the target lymphocyte recognizes the unique antigen by binding the unique antigen or by binding one or more molecular complexes comprising the unique antigen. In some embodiments, the detecting further comprises applying, by a processor, a nearest neighbor decoding algorithm configured to determine the unique antigen that is specific to the lymphocyte receptor chain sequence. In some embodiments, the detecting further comprises: applying, by a processor, a decoding algorithm, wherein the decoding algorithm is configured to detect the one or more antigens that are specific to the lymphocyte receptor chain sequence when the lymphocyte cell receptor chain sequence is not substantially present in at least one reaction mixture of the unique subset of the plurality of reaction mixtures, and wherein the at least one reaction mixture comprises the one or more antigens.

In another aspect, the invention provides for a method for determining a lymphocyte cell receptor chain sequence, or a portion thereof, specific for one or more antigens, comprising: sorting a plurality of antigens into a plurality of reaction mixtures, wherein the sorting comprises adding at least two unique antigens of the plurality of antigens to at least two unique subsets of the plurality of reaction mixtures such that the at least two unique antigens are not added to any two identical subsets of the plurality of reaction mixtures, and wherein the at least two unique subsets are configured to allow a detection of one or more antigens that are specific to the lymphocyte cell receptor chain sequence, contacting each reaction mixture with a biological sample comprising a plurality of lymphocytes, separating a target lymphocyte from a subset of the plurality of lymphocytes, wherein the target lymphocyte reacts with the at least one antigen of the plurality of antigens, sequencing nucleic acids of the target lymphocyte to obtain the lymphocyte cell receptor chain sequence, and applying, using a processor, a nearest neighbor decoding algorithm configured to detect specificity of the lymphocyte cell receptor chain sequence to the one or more antigens.

In some embodiments, the lymphocyte is a T cell or a B cell. In some embodiments, the lymphocyte cell receptor chain sequence comprises a receptor chain sequence pair, and wherein the receptor chain sequence pair consists of two components of a receptor of the target lymphocyte. In some embodiments, the method further comprising contacting at least one reaction mixture of the plurality of reaction mixtures with a query antigen.

TCR Promiscuity

In some embodiments, superimposed codes are used to separate peptides/antigens into antigen pools at step 201 which allows the assay to detect which peptides/antigens are recognized by a single LCR chain sequence when it recognizes more than one peptide/antigen. An example of a superimposed code is a Zatocoding (see Mooers, C. N., and Ashby, W. R., incorporated by reference in its entirety herein).

In some embodiments, superimposed codes are applied to assign each antigen (e.g., peptide) to n antigen pools that are unique to the antigen. If N is the total number of antigen pools utilized, then a given antigen is assigned to a subset of these antigen pools n, where n<N. In some embodiments, preferably n is equal to F*N, where F is the fraction of antigen pools that are optimal. In some embodiments, the binary number corresponding to the pools that an antigen is assigned to is the code word of that antigen, where a pool in which it is present is assigned a "1" and a pool where it is absent is assigned a "0", and these binary digits are concatenated to form the antigen's code word (e.g., for five pools, inclusion in pools 1 and 3, and exclusion in pools 2, 4, and 5 would result in the binary number "10100"). The fraction of antigen pools F is typically $1-2^{-1/r}$ r where r is the desired detection ability of a given TCR chain sequence to recognize r antigens. Table 1 provides the fraction, F, of the total number of antigen pools, N, that should be used for a given antigen according the equation above.

TABLE 1

| r (Number of antigens expected to be recognized by a typical LCR) | F (Fraction of antigen pools assigned to each antigen) |
|---|---|
| 1 | .5 |
| 2 | .293 |
| 3 | .205 |
| 4 | .159 |

In some embodiments, each antigen (e.g., peptide) is randomly assigned to F*N antigen pools, except that it is ensured that no two antigens are allocated to exactly the same group of antigen pools. In some embodiments, an antigen's code word describes the pools in which it is present and absent, where "1" represents a pool where it is present and "0" represents a pool where it is absent. These binary digits are concatenated in pool number order (e.g., the antigen code word "01100" means the antigen is present in pools 2 and 3, and not present in pools 1, 4, and 5). In some embodiments, the assignment of antigens to antigen pools (e.g., their code words) is recorded. In some embodiments, for a LCR chain sequence observed in the sequencing of an antigen pool's desired positive selected component (e.g., CD8+ Activated), the sequence's enrichment is computed versus its presence in the sequencing data from the negative selection of this pool (e.g., CD8+ Not Activated). In some embodiments, for a LCR chain sequence observed in the sequencing of an antigen pool's desired positive selected component, the sequence's enrichment is computed versus its presence in the sequencing data from other antigen pools. In some embodiments, LCR chain sequence enrichment is computed based on read counts. In some embodiments, enrichment is computed based on read counts as corrected by UMIs as known in the art. In some embodiments, LCR chain sequence enrichment is computed based on cell counts. In some embodiments, pool specific LCR chain sequence enrichment is computed as described herein.

In some embodiments, if a LCR chain sequence is enriched in a number of antigen pools that is larger than $r*F*N$, then the LCR chain sequence is flagged as recognizing more than r antigens. In some embodiments, for each antigen, the antigen pools it was assigned to are evaluated for enriched LCR chain sequences. In some embodiments, when all of the pools corresponding to an antigen's assignment are enriched for a LCR chain sequence as described herein, then the LCR chain sequence is output as recognizing the antigen. The false positive rate of the assay is expected to be bounded by $(\frac{1}{2})^n$ when r is an accurate estimate. Thus, when n is more than about 3, the false positive rate should be small. In some embodiments, to reduce the error rate, N is increased which causes a corresponding increase in n to lower the false positive rate to a desired level. The receptor sequence pairing of LCR chain sequences (T cell alpha and beta, B cell heavy and light) is accomplished as described herein for paired chains that are assigned to the same antigen or antigens. Rank comparisons of read counts for pairing receptor chain sequences is done for each antigen separately.

In some embodiments, a binary number corresponding to the enrichment of an LCR chain sequence is constructed by concatenating its enriched ("1") and non-enriched ("0") pools (e.g., "10101" corresponds to an LCR chain sequence enriched in pools 1, 3, and 5, and not enriched in pools 2 and 4). The Hamming distance of this binary number is computed with respect to the result of the "OR" of the code words for each possible combination of the antigens. In some embodiments, a nearest neighbor decoding algorithm is used, and if there is a unique nearest neighbor in Hamming distance between the binary number and the Boolean bitwise "OR" of a combination of antigen code words, the decoding method outputs this as the combination of antigens that are recognized by the LCR chain sequence. For example, if there are K antigens, the method considers all $2^K$ possible "OR" combinations of antigen code words, including single code words, all combinations of 2 code words, all combinations of 3 code words, and so on. This method allows decoding in situations where an LCR chain sequence is specific to more than one antigen (e.g., by computing a Hamming distance for a set of combined code words). In some embodiments, antigens are only considered in combinations if their code words have a minimum number of "1" bits that are also present in the binary number being decoded. In some embodiments, if there are K antigens, the method considers all $$\sum_{j=1}^{r}\binom{K}{j}$$

possible "OR" combinations of antigen code words from up to r antigens (where r is the number of antigens expected to be recognized by a typical LCR used during encoding). In some embodiments, other distance metrics (e.g., Euclidean distance, cosine distance) are used to compute nearest neighbors. In some embodiments, if there is not a unique nearest neighbor, the decoding method outputs an error.

Nearest Neighbor Decoding Algorithm

In some embodiments, nearest neighbors decoding consists of the following computational steps.

In some embodiments, the inputs for the computation are:

N: Number of antigen pools.

K: Number of antigens.

$E_{1, \ldots, N}$: The observed enrichment (enriched: "1"; non-enriched: "0") of an LCR chain sequence in each of the N antigen pools.

$C_{1, \ldots, K}$: Matrix of code words for each of K antigens where $C_i$ specifies a binary number corresponding to the antigen pools where antigen i is present. The binary digits are concatenated in pool number order, where "1" represents a pool where the antigen is present, and "0" represents a pool where it is absent.

m: Threshold minimum number of antigen pools overlapping with the observed enrichment to consider an antigen for "OR" combinations during superimposed decoding.

Neighbor-Distance: A distance function (e.g., Hamming distance, Euclidean distance, cosine distance) used to compute the distance between two code words. This function takes in two code words represented as binary numbers and outputs an integer distance. In some embodiments, generalized minimum distance decoding or maximum likelihood decoding can be used for neighbor distance functions as is known in the art.

From the input pool enrichments $E_{1, \ldots, N}$, for a given LCR chain sequence, a corresponding binary number sequence B is constructed by concatenating the enriched ("1") and non-enriched ("0") pools for the LCR chain sequence. The binary digits are concatenated in pool number order, where "1" represents a pool where the antigen is present, and "0" represents a pool where it is absent (e.g., B="10101" which corresponds to an LCR chain sequence enriched in pools 1, 3, and 5, and not enriched in pools 2 and 4).

Next, a set of basis code words W is computed for the purpose of decoding. In some embodiments, if antigens were distributed into antigen pools using an error-correcting code (e.g., a Hamming(7,4) code), then $W=U_i C_i$ (where W is the union of all code words in C and i is a given antigen). In some embodiments, if antigens were distributed into antigen pools using a superimposed code (e.g., a zatocoding), W is the union of all $2^K$ possible bit-wise Boolean "OR" combinations of antigen code words in C, including single code words, all combinations of 2 code words, all combinations of 3 code words, and so on, and each base code word in W is annotated by the combination of antigen code words used to create it. For example, if $C_1$ is "11000" and $C_2$ is "00101" then the combination of $C_1$ and $C_2$ would be represented by "11101" in W which is the bit-wise "OR" of the two code words, and "11101" would be annotated as the combination $C_1$ and $C_2$. In some embodiments, antigens are only considered in combinations if their code words have at least m "1" bits that are also present in B. In some embodiments, W does not include combinations of antigen code words for more than r antigens at once, and thus the number of possible "OR" combinations of antigen code words from up to r antigens is $$\sum_{j=1}^{r}\binom{K}{j}$$

(where r is the number of antigens expected to be recognized by a typical LCR used during encoding). For each basis code word, W stores both the binary code word and its annotation of the one or more antigens that correspond to the basis code word.

Next, the distances $d_1, \ldots, d_j$ between B and all basis code words $1, \ldots, j$ in W are computed using the Neighbor-Distance function. For example, if the Neighbor-Distance function uses a Hamming distance, the Neighbor-Distance is the number of positions in a code word sequence in which the two code words differ. For N pools, a code word has N positions. For N=5, if B=00111 (first code word) and $W_1$=11000 (second code word), then $d_1$=5 (the maximum possible Hamming distance for N=5). If B=00111 (first code word) and $W_2$=00110 (second code word), then $d_2$=1. Let z be the minimum of $d_1, \ldots, d_j$. If there is not a unique distance with minimum distance z, the output will be an error ("ERROR"). Otherwise, the output will be the annotated basis antigen(s) in $W_i$ corresponding to basis code word with distance z. The output may consist of a single antigen or multiple antigens that were combined using "OR" to form basis code word $W_i$. If the output consists of multiple antigens, the LCR chain sequence is specific to more than one antigen.

Host T Cell Activation and Non-Specific Markers

In some embodiments, a separate control pool is established that contains no antigens/peptides ("Control Pool 0"; see FIG. 2). This pool is separated at step 203, as are the other pools, and is used to detect cells that are activated when they are retrieved from a donor. In some embodiments, donor cells are derived from humans or animals. LCR chain sequences that are found in the separated active set of cells in the control pool represent LCR chain sequences that correspond to host activated cells or cells that contain AIM markers that are not induced by the antigens/peptides in the other pools (i.e., the antigen pools). In some embodiments, these LCR chain sequences can be eliminated from the antigen specific set of LCR chain sequences discovered in the remainder of the antigen pools.

LCR Chain Sequence Count Calibration

In some embodiments, control antigens (e.g., control peptides) can be added to target antigens of interest to calibrate the assay across donors. Control antigens that are broadly present in the human population can be derived from common immunizations such as measles, mumps, rubella, polio, and other control antigens/peptides can be used in addition to antigens specific to a target of interest. In some embodiments, a threshold level of detection of the control antigens in a representative human population can be predetermined. In some embodiments, added control antigens (e.g., control peptides) are based on vaccine components that have been used to immunize donors. In some embodiments, control peptides are added to the list of target antigens to form a complete set of K antigens/peptides to be assayed (e.g., peptide 1-K can include one or more target peptides and one or more control peptides).

In some embodiments, the counts of LCR chain sequences for control antigens can be used to normalize counts for other antigens to provide comparable figures across PBMC samples. In some embodiments, normalization is accomplished by adjusting the LCR chain sequence counts in a given sample for an antigen to be presented as a ratio of the antigen's counts divided by the sum of the control antigen counts.

Correcting for Experimental Noise

In some embodiments, antigens are distributed into antigen pools based on a minimum Hamming distance between the binary encoding of pools where they reside as described in this disclosure (e.g., using a Hamming(7,4) code; see FIG. 1). In some embodiments, codes for asymmetric channels can be used when the chance of a "1" occurring by error is higher than the chance of a "0" occurring by error such as when a T cell recognized more than one antigen (see Kim and Freiman, 1959, for examples of asymmetric codes). In some embodiments, other error correcting codes can be employed as known in the art.

The devices, systems, and methods disclosed herein are not to be limited in scope to the specific embodiments described herein. Indeed, various modifications of the devices, systems, and methods in addition to those described will become apparent to those of skill in the art from the foregoing description.

What is claimed is:

1. A method for determining a lymphocyte cell receptor chain sequence, or a portion thereof, specific for at least two or more unique antigens, the method comprising:
    sorting a plurality of antigens into a plurality of reaction mixtures, wherein the sorting comprises adding the at least two unique antigens of the plurality of antigens to at least two unique subsets of the plurality of reaction mixtures such that the at least two unique antigens are not added to any two identical subsets of the plurality of reaction mixtures, and wherein the at least two unique subsets are configured to allow a detection of the at least two or more unique antigens that are specific to the lymphocyte cell receptor chain sequence;
    contacting each reaction mixture of the plurality of reaction mixtures with a biological sample comprising a plurality of lymphocytes;
    separating a target lymphocyte from a subset of the plurality of lymphocytes, wherein the target lymphocyte recognizes the at least two unique antigens of the plurality of antigens;
    sequencing nucleic acids of the target lymphocyte to obtain the lymphocyte cell receptor chain sequence; and
    detecting the at least two or more unique antigens that are specific to the lymphocyte cell receptor chain sequence.

2. The method of claim 1, wherein the lymphocyte is a T cell or a B cell.

3. The method of claim 1, wherein separating the target lymphocyte is performed using multimer sorting.

4. The method of claim 1, wherein the target lymphocyte is a T cell, and wherein separating the T cell is based on a marker selected from the group consisting of CD3, CD4, CD8, CD137, OX40, CD25, PD-L1, CD69, and CD154.

5. The method of claim 1, wherein the lymphocyte cell receptor chain sequence comprises a receptor chain sequence pair, and wherein the receptor chain sequence pair consists of two components of a receptor of the target lymphocyte.

6. The method of claim 1, wherein a number of reaction mixtures comprising the at least two unique subsets is a function of a number of expected antigens that are specific to the lymphocyte cell receptor chain sequence.

7. The method of claim 1, wherein the plurality of reaction mixtures comprises at least one control reaction mixture, and wherein the control reaction mixture does not contain any antigens that are added to the biological sample.

8. The method of claim 1, wherein the target lymphocyte recognizes the at least two unique antigens of the plurality of antigens by binding the at least two unique antigens of the plurality of antigens or by binding two or more molecular complexes comprising the at least two or more unique antigens of the plurality of antigens.

9. The method of claim 1, wherein the detecting further comprises applying, by a processor, a nearest neighbor decoding algorithm configured to determine the at least two or more unique antigens that are specific to the lymphocyte cell receptor chain sequence.

10. The method of claim 1, wherein the detecting further comprises:
applying, by a processor, a decoding algorithm, wherein the decoding algorithm is configured to detect the at least two or more unique antigens that are specific to the lymphocyte cell receptor chain sequence when the lymphocyte cell receptor chain sequence is not substantially present in at least one reaction mixture of the at least two unique subsets of the plurality of reaction mixtures.

11. The method of claim 1, further comprising assigning a superimposed code to each antigen of the plurality of antigens, wherein the superimposed code is configured to allow a detection of the at least two or more unique antigens that are specific to the lymphocyte cell receptor chain sequence.

12. A method for determining a lymphocyte cell receptor chain sequence, or a portion thereof, specific for at least two or more unique antigens, the method comprising:
sorting a plurality of antigens into a plurality of reaction mixtures, wherein the sorting comprises adding the at least two unique antigens of the plurality of antigens to at least two unique subsets of the plurality of reaction mixtures such that the at least two unique antigens are not added to any two identical subsets of the plurality of reaction mixtures, and wherein the at least two unique subsets are configured to allow a detection of the at least two or more unique antigens that are specific to the lymphocyte cell receptor chain sequence;
contacting each reaction mixture with a biological sample comprising a plurality of lymphocytes;
separating a target lymphocyte from a subset of the plurality of lymphocytes, wherein the target lymphocyte reacts with the at least two unique antigens of the plurality of antigens;
sequencing nucleic acids of the target lymphocyte to obtain the lymphocyte cell receptor chain sequence; and
applying, using a processor, a nearest neighbor decoding algorithm configured to detect specificity of the lymphocyte cell receptor chain sequence to the at least two or more antigens.

13. The method of claim 12, wherein the lymphocyte is a T cell or a B cell.

14. The method of claim 12, wherein the lymphocyte cell receptor chain sequence comprises a receptor chain sequence pair, and wherein the receptor chain sequence pair consists of two components of a receptor of the target lymphocyte.

15. The method of claim 12, further comprising contacting at least one reaction mixture of the plurality of reaction mixtures with a query antigen.

* * * * *